United States Patent [19]

Sakurai

[11] 4,329,991
[45] May 18, 1982

[54] TAMPON

[75] Inventor: Akira Sakurai, Utsunomiya, Japan

[73] Assignee: Kao Soap Co., Ltd., Tokyo, Japan

[21] Appl. No.: 183,873

[22] Filed: Sep. 4, 1980

[30] Foreign Application Priority Data

Oct. 17, 1979 [JP] Japan .......................... 54-143539[U]

[51] Int. Cl.³ ............................................ A61F 15/00
[52] U.S. Cl. .................................................. 128/263
[58] Field of Search ........................ 128/263, 270, 285

[56] References Cited

U.S. PATENT DOCUMENTS 2,829,646  4/1958  Kurkjian .............................. 128/263
4,273,125  6/1981  Sakurai ................................ 128/263

Primary Examiner—C. Fred Rosenbaum
Attorney, Agent, or Firm—Blanchard, Flynn, Thiel, Boutell & Tanis

[57] ABSTRACT

A tampon is disclosed comprising an outer cylinder, a push-out portion which is slidingly fitted into the outer cylinder from the rear end thereof and is adapted to be pushed towards the forward end of the outer cylinder, and an absorbing member contained in said outer cylinder, wherein at least one hole is formed on the outer cylinder at a position behind the absorbing member. The push-out portion is formed by a cylinder having at least one push-out piece having a width slightly smaller than the length of the hole on the outer cylinder in the circumferential direction, the number of the push-out pieces being the same as the number of the holes in the outer cylinder. Before application of the tampon, the push-out piece is kept in contact with the outer face of the outer cylinder by being inserted through the hole in the outer cylinder. When the tampon is actually used, the push-out piece is withdrawn into the outer cylinder and then pushed forward to push out the absorbing member contained therein through an opening at the forward end of the outer cylinder.

6 Claims, 3 Drawing Figures

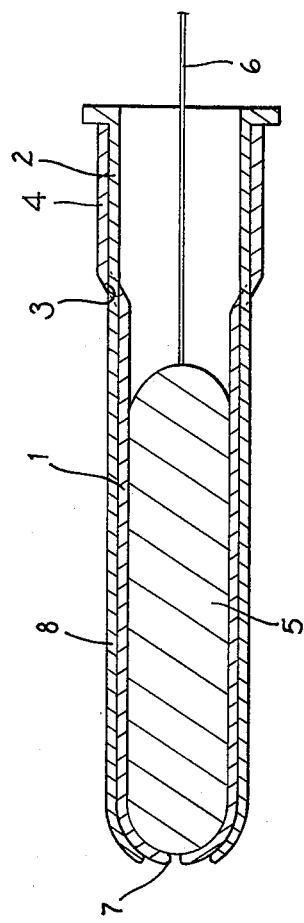
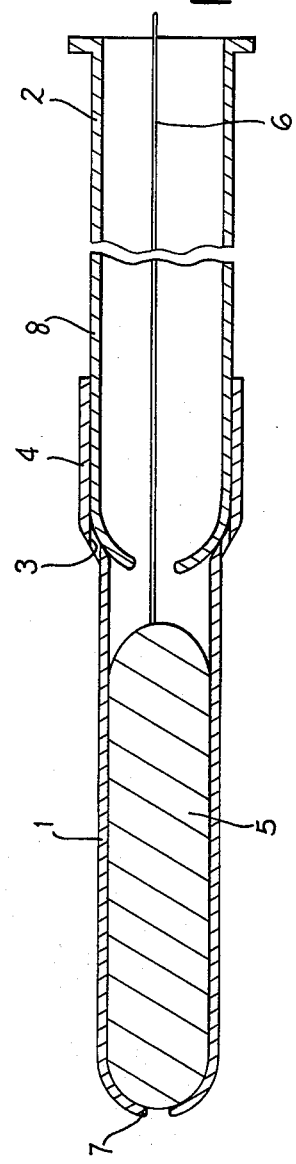
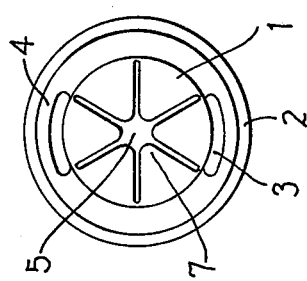

TAMPON

The present invention relates to a sanitary tampon. More particularly, the present device relates to a sanitary tampon characterized in that before application, a push-out piece is held on and kept in contact with the outer surface of an outer cylinder and extends through a hole formed on the outer cylinder. When the tampon is actually used, the push-out piece is withdrawn completely into the outer cylinder and acts as a push-out member.

Sanitary napkins have heretofore mainly been used as sanitary articles, but the demand for tampon type sanitary articles has recently been increasing. Various types of tampons, such as those mentioned below, have been devised as sanitary tampons in order to satisfy this demand.

(1) Finger Type

Typically, there is used an absorbing member formed by compression molding of an absorbent material such as absorbent cotton or rayon. A tampon of the finger type is characterized in that at the time of application, an envelope covering the absorbing member is completely removed and the absorbing member is inserted into the body by the fingers of a user. The greatest advantage of the sanitary article of this type is that the size of the sanitary article is reduced. More specifically, the sanitary article of this kind is much smaller than an ordinary napkin, and the sanitary article of this type is advantageous in that it can be carried about easily, for example, in a handbag or the like. However, as pointed out before, the absorbing member to be inserted must inevitably be touched the user's fingers, and from the sanitary viewpoint, the sanitary article of this type is disadvantageous in that the absorbing member must be inserted by fingers that inevitably come into contact with body areas before insertion.

(2) Stick Type

In stick-type tampons, there is used an absorbing member such as mentioned in (1) above. An appropriate hole is formed in the tail portion and one end of a stick-like applicator formed from paper or the like is set in this hole. Then, the stick-like applicator is held by the hand and the absorbing member is inserted into the body. From the sanitary viewpoint, the sanitary article of this type is improved over the sanitary article of the type (1). However, since the absorbing member is inserted by a stick which is much smaller in diameter than the absorbing member, the insertion operation is unstable and the user has an uneasy feeling.

(3) Application Type

In this tampon, there is used an insertion tool comprising outer and inner cylinders composed and formed of a paper, a plastic material or the like, which optionally slide relative to each other. An absorbing member contained in the outer cylinder is pushed out and inserted into the body from the opening on the top end of the outer cylinder by the sliding movement of the inner cylinder. The sanitary problem involed in the sanitary article of the type (1) is substantially solved by this arrangement. However, the sanitary article of this type is defective in that (1) separation of the cylinders occurs readily because fitting between the cylinders is not appropriate and (2) the entire length of the sanitary article becomes large, and is more than 2 times the length of the absorbing member because the above-mentioned inserting tool is inevitably used.

The tampon of the present invention belongs to the type (3). The present device relates to an improvement in the sanitary tampon having a mechanism for inserting an absorbing member by use of an inserting tool. It is a primary object of the present invention to provide a tampon of the applicator type in which the above-mentioned defects are eliminated. More specifically, the primary object of the present device is to provide a tampon characterized in that (i) the tampon is excellent from the sanitary viewpoint, (ii) separation of the outer and inner cylinders is prevented while the tampon is carried about, (iii) the size is reduced and (iv) the tampon is excellent in the feeling given to a user when it is actually applied.

In accordance with the present invention, there is provided a tampon comprising an applicator including an outer cylinder, a push-out portion which is slidingly receivable into the outer cylinder from the rear end thereof and which can be pushed toward the front end of the outer cylinder, and an absorbing member contained the front portion of said outer cylinder. At least one hole is formed in the outer cylinder at a position located a distance from the front end of the outer cylinder which is greater than the length of the absorbing member. The push-out portion is formed of a cylinder having at least one push-out piece having a width slightly less than the circumferential length of a hole on the outer cylinder so that it can be moved through this hole. The number of said push-out piece is the same as the number of the holes in the outer cylinder. Before application of the tampon, the end of the push-out piece nearest the front end of the outer cylinder is kept in contact with the outer face of the outer cylinder by being extended through the hole of the outer cylinder while at the same time the rear portions of the push-out member is inside the outer cylinder. When the tampon is actually used, the push-out piece is withdrawn through the hole so that it is received into the outer cylinder and then the push-out piece is moved frontwardly to push out the absorbing member contained therein.

In the tampon of the present invention, since the push-out piece is removably fitted and fixed to the outer cylinder through the hole formed in the outer cylinder and is thus in part kept in contact with the outer surface of the outer cylinder before application, the length of the applicator is only slightly larger than the length of the absorbing member, and the total size of the tampon is much smaller than the size of a conventional tampon of the applicator type. Furthermore, when the tampon is actually used, the push-out piece of the push-out portion is caused to slide rearwardly so that it is withdrawn from the hole of the outer cylinder and is received inside the outer cylinder. The push-out portion is then caused to slide forwardly to push out the absorbing member. Accordingly, the insertion operation can be remarkably facilitated.

BRIEF DESCRIPTION OF THE DRAWINGS

FIG. 1 is a sectional view illustrating one embodiment of the tampon of the present invention.

FIG. 2 is a sectional view illustrating the state of the tampon of the present device just before insertion.

FIG. 3 is a front view of the tampon in the state illustrated in FIG. 2.

In the drawings the reference numbers identify parts as follows: 1 is the outer cylinder; 2 is the push-out portion; 3 are holes of the outer cylinder; 4 is the supporting portion of the outer cylinder; 5 is the absorbing member; 6 is the take-out string; 7 is the front end of the outer cylinder; and 8 is the push-out piece.

The present device will now be described in detail with reference to one preferred embodiment illustrated in the accompanying drawings.

FIG. 1 is a sectional view illustrating one embodiment of the tampon according to the present invention.

As shown in FIG. 1, at least one circumferentially elongated hole 3 is formed in the outer cylinder 1 at a position spaced a distance from the front end 7 greater than the length of the absorbing member 5. It is preferred that the front end 7 of the outer cyliner 1 has a spherical surface consisting of a plurality of split pieces, because such an arrangement reduces the resistance to insertion into the vagina. If the diameter of the outer cylinder 1 rearwardly of the hole 3 is larger than the diameter of the outer cylinder 1 in front of the hole 3, the flexural stress imposed on the hole 3 by the push-out piece 8 before application is moderated. Furthermore, in such a case, since the diameter of the supporting portion 4 of the outer cylinder 1 is greater, the user does not get an uneasy feeling when the tampon is actually applied.

The push-out portion 2 of the applicator of the invention comprises a cylinder and at least one push-out piece 8 extends longitudinally along the tampon from said cylinder. The push-out piece 8 has a width slightly smaller than the circumferential length of the hole 3 provided in the outer cylinder 1. The number of the push-out pieces 8 should be the same as the number of the holes 3 and is preferred to be two. It is preferred that the front end portion of the push-out piece 8 is inwardly curved so that the front end of the push-out piece 8 contacts the outer surface of the front end 7 of the outer cylinder 1.

In the tampon of the present invention, before application, in which the parts are positioned as shown in FIG. 1, the push-out piece 8 is removably fitted and fixed to the outer surface of the outer cylinder 1 by extending through the hole 3 formed thereon so that the push-out piece 8 is kept in contact with the outer surface of the outer cylinder 1, and the absorbing member 5 is contained in the outer cylinder 1.

When the tampon of the present device is actually used, the push-out portion 2 is first caused to slide backwardly while the supporting portion 4 of the outer cylinder is held in position, as shown in FIG. 2. The push-out piece 8 thereby slides along the outer side of the outer cylinder 1 in the portion in front of the hole 3 and along the inner side of the supporting portion 4 of the outer cylinder 1 in the portion behind the hole 3, whereby the push-out piece 8 is withdrawn from the hole 3 and is received in the outer cylinder 1. In this case, since the entire circumference of the supporting portion 4 supports the push-out piece 8, the operation can be performed very stably. The outer cylinder 1 is then inserted into the vagina and the push-out portion 2 is pushed frontwardly. The tail portion of the absorbing member 5 is pushed by the front end of the push-out piece 8 and is moved into the body through the front open portion of the outer cylinder 1. Thus, the absorbing member 5 is completely pushed out from the outer cylinder 1 and the inserting operation is completed.

The applicator used for the tampon of the present device may be formed from an appropriate material such as a paper or plastic material as in case of conventional tampons, and the material used to make the applicator is not particularly critical in the present device.

In the preparation of conventional tampons, the absorbing member should be packed only from the front end portion thereof. In contrast, in the present device, the absorbing member can be packed from either the front end portion or the rear portion, and since it is possible to pack the absorbing member from the rear portion in one step, the process can be remarkably facilitated.

As will be apparent from the foregoing illustration, the tampon of the present invention having the above-mentioned structure is kept sanitary before application and no trouble is caused by insufficient connection between the outer and inner cylinders. Furthermore, the size of the tampon of the present device is reduced to about ½ of the size of the conventional tampon of the applicator type, and the problem of large bulk when the tampon is carried about is eliminated. When the tampon of the present device is actually used, the tampon can be applied by a simple operation of sliding backward the portion for pushing out the absorbing member. Accordingly, the tampon of the present invention is very convenient to use.

What is claimed is:

1. A tampon, comprising:

an elongated outer member having a rear portion and a front cylindrical portion which is adapted to be inserted into a vagina, said rear portion being laterally enlarged relative to said front cylindrical portion, and a wall extending laterally outwardly from the rear end of said front cylindrical portion to the front end of said rear portion, said wall having one or more holes therethrough;

a mass of absorbent material disposed inside said front cylindrical portion close to the front end thereof and adapted to be moved through said front end of said front cylindrical portion into a vagina;

a push-out member mounted on said elongated outer member for sliding movement in a direction lengthwise thereof, said push-out member having a rear portion slidably disposed inside said rear portion of said elongated outer member, said push-out member having one or more longitudinally extending push-out pieces corresponding in number to the number of said holes, said push-out piece extending from said rear portion of said push-out member through its associated hole in said elongated outer member and thence forwardly along the outer surface of said front cylindrical portion of said elongated outer member, said push-out piece being receivable inside said elongated outer member when said push-out member is moved longitudinally rearwardly relative to said elongated outer member such that subsequent longitudinal movement of said push-out member in a direction toward the front end of said front cylindrical portion causes said push-out piece to move said mass of absorbent material out of said front cylindrical portion through the front end thereof.

2. A tampon as claimed in claim 1 wherein said front end of said front cylindrical portion has a partially spherical, convex surface, said partially spherical, convex surface having a plurality of radial slits radiating from a central opening so that said partially spherical, convex surface is defined by a plurality of flexible pieces, and the front end of said push-out piece is inwardly curved so that it engages said partially spherical, convex surface of said front cylindrical portion.

3. A tampon as claimed in claim 1 or claim 2 wherein said wall is located rearwardly of the rear end of said mass of absorbent material.

4. A tampon as claimed in claim 1 or claim 2 wherein said wall has two holes therethrough and said push-out member has two push-out pieces corresponding to said holes.

5. A tampon as claimed in claim 1 wherein said hole is elongated in the circumferential direction of said front cylindrical portion, the length of said hole being slightly greater than the width of said push-out piece.

6. A tampon as claimed in claim 1 or claim 2 wherein said rear portion of said push-out member is a cylinder and said rear portion of said elongated outer member is a cylinder which has a larger internal diameter than the external diameter of said rear portion of said push-out member so that said rear portion of said push-out member is closely slidably sleeved within said rear portion of said elongated outer member.

* * * * *